(12) United States Patent
Tsujikawa (10) Patent No.: US 10,914,883 B2
(45) Date of Patent: Feb. 9, 2021

(54) IMAGING APPARATUS INCLUDING ILLUMINATING LIGHT GUIDE WITH POSITIONING FEATURES

(71) Applicant: FUJITSU FRONTECH LIMITED, Tokyo (JP)

(72) Inventor: Akinori Tsujikawa, Inagi (JP)

(73) Assignee: FUJITSU FRONTECH LIMITED, Inagi (JP)

(*) Notice: Subject to any disclaimer, the term of this patent is extended or adjusted under 35 U.S.C. 154(b) by 162 days.

(21) Appl. No.: 16/207,845

(22) Filed: Dec. 3, 2018

(65) Prior Publication Data

US 2019/0101680 A1 Apr. 4, 2019

Related U.S. Application Data

(63) Continuation of application No. PCT/JP2016/067780, filed on Jun. 15, 2016.

(51) Int. Cl.
*G06K 9/00* (2006.01)
*F21V 8/00* (2006.01)
(Continued)

(52) U.S. Cl.
CPC .......... *G02B 6/0001* (2013.01); *A61B 5/1171* (2016.02); *G03B 15/02* (2013.01); *G03B 15/03* (2013.01); *G03B 15/14* (2013.01); *G03B 17/02* (2013.01); *G06T 1/00* (2013.01); *H04N 5/225* (2013.01); *H04N 5/2252* (2013.01); *H04N 5/2254* (2013.01); *H04N 5/2256* (2013.01); *A61B 2562/0233* (2013.01); *A61B 2562/16* (2013.01)

(58) Field of Classification Search
CPC ........ G06K 2009/00932; G02B 6/0088; G02F 1/133615
See application file for complete search history.

(56) References Cited

U.S. PATENT DOCUMENTS 4,281,895 A * 8/1981 Mohr ..................... G02B 7/007
359/827
5,988,827 A * 11/1999 Lee ........................ G01D 11/28
362/633

(Continued)

FOREIGN PATENT DOCUMENTS

CN 105072998 A 11/2015
EP 1830123 A1 9/2007
(Continued)

OTHER PUBLICATIONS

EESR issued in corresponding EP patent application No. 16905457.4, dated Apr. 23, 2019.
(Continued)

*Primary Examiner* — Ismael Negron
(74) *Attorney, Agent, or Firm* — Greer Burns & Crain Ltd.

(57) ABSTRACT

An imaging apparatus includes an imaging element, a lens unit that focuses light on the imaging element, a light source located around the lens unit, a light guide body that surrounds the lens unit and that guides light emitted from the light source, and a framing member surrounding the light guide body, wherein the light guide body includes an engagement concave part that engages an engagement convex part of the framing member.

5 Claims, 8 Drawing Sheets

(51) Int. Cl.
*G03B 17/02* (2021.01)
*G06T 1/00* (2006.01)
*H04N 5/225* (2006.01)
*G03B 15/02* (2021.01)
*A61B 5/1171* (2016.01)
*G03B 15/03* (2021.01)
*G03B 15/14* (2021.01)

(56) References Cited

U.S. PATENT DOCUMENTS

| | | | | |
|---|---|---|---|---|
| 6,020,583 | A * | 2/2000 | Walowit | G01J 3/0251 |
| | | | | 250/226 |
| 6,554,452 | B1 * | 4/2003 | Bourn | G01N 21/8806 |
| | | | | 313/113 |
| 6,595,651 | B2 * | 7/2003 | Jeong | G02B 6/0068 |
| | | | | 349/65 |
| 6,820,992 | B2 * | 11/2004 | Yu | G02B 6/0088 |
| | | | | 349/65 |
| 7,646,423 | B2 * | 1/2010 | Yoshida | G06K 9/00033 |
| | | | | 348/370 |
| 7,690,827 | B2 * | 4/2010 | Matsuo | G06K 9/2027 |
| | | | | 362/558 |
| 9,736,343 | B2 * | 8/2017 | Tsujikawa | G03B 11/045 |
| 10,321,027 | B2 * | 6/2019 | Tsujikawa | H05K 7/1404 |
| 2002/0191075 | A1 | 12/2002 | Doi et al. | |
| 2007/0206391 | A1 | 9/2007 | Matsuo et al. | |
| 2010/0119122 | A1 * | 5/2010 | Nakayama | A61B 5/1172 |
| | | | | 382/115 |
| 2013/0329031 | A1 * | 12/2013 | Miura | G06K 9/2018 |
| | | | | 348/77 |
| 2016/0014308 | A1 | 1/2016 | Yamazaki et al. | |
| 2016/0044214 | A1 | 2/2016 | Tsujikawa | |
| 2016/0044215 | A1 | 2/2016 | Tsujikawa et al. | |
| 2019/0094657 | A1 * | 3/2019 | Tsujikawa | G01S 7/4816 |

FOREIGN PATENT DOCUMENTS

| | | |
|---|---|---|
| JP | 08313778 A | 11/1996 |
| JP | 2002122899 A | 4/2002 |
| JP | 2007052326 A | 3/2007 |
| JP | 2008180916 A | 8/2008 |
| JP | 4708220 B2 | 3/2011 |
| WO | 2014162388 A1 | 10/2014 |
| WO | 2014196044 A1 | 12/2014 |

OTHER PUBLICATIONS

Written Opinion of the International Searching Authority of PCT/JP2016/067780, dated Sep. 13, 2016 (partial English translation).
Int'l. Search Report issued in Int'l. Application No. PCT/JP2016/067780, dated Sep. 13, 2016.
Office action issued in corresponding Japanese patent application No. 2018-523102, dated Sep. 10, 2019 (with full machine translation).
Office action issued in corresponding Chinese patent application No. 201680086504.7, dated Jun. 5, 2020 (with translation).

* cited by examiner

IMAGING APPARATUS INCLUDING ILLUMINATING LIGHT GUIDE WITH POSITIONING FEATURES

CROSS-REFERENCE TO RELATED APPLICATION

This application is continuation application of International Application PCT/JP2016/067780 filed on Jun. 15 2016 and designated the U.S., the entire contents of which are incorporated herein by reference.

TECHNICAL FIELD

The present invention relates to an imaging apparatus.

BACKGROUND ART

Conventionally, an imaging apparatus that includes an imaging element disposed on a wiring board, a lens unit that focuses light on the imaging element, and a light source disposed around the lens unit has been used for a biometrics authentication apparatus that performs authentication based on biological information such as palm or finger veins, fingerprints, or pupil irises. As such an imaging apparatus, a known imaging apparatus further includes a light guide body that surrounds a lens unit and that guides light emitted from a light source, wherein an engagement convex part is provided on the side surface of the light guide body (see, for example, Japanese Patent Number 4708220).

SUMMARY OF THE INVENTION

A disclosed imaging apparatus includes an imaging element, a lens unit that focuses light on the imaging element, a light source located around the lens unit, a light guide body that surrounds the lens unit and that guides light emitted from the light source, and a framing member surrounding the light guide body, wherein the light guide body includes an engagement concave part that engages an engagement convex part of the framing member.

EMBODIMENTS

In the meantime, a light guide body is a member for guiding light and is thus formed of a material such as acryl that is easily damaged. Hence, if the imaging apparatus is subject to a dropping impact, an engagement convex part provided as described above on a side surface of a light guide body could be damaged.

A smaller projection of the engagement convex part makes engagement with another member of the light guide body more easily weakened when the engagement convex part is damaged.

The following describes an imaging apparatus 1 in accordance with an embodiment by referring to the drawings.

The imaging apparatus 1 emits light to a subject (e.g., a palm) and receives, at an imaging element 91, the light reflected from the subject so as to capture an image. The imaging element 91 is, for example, an image sensor.

Figure 1:
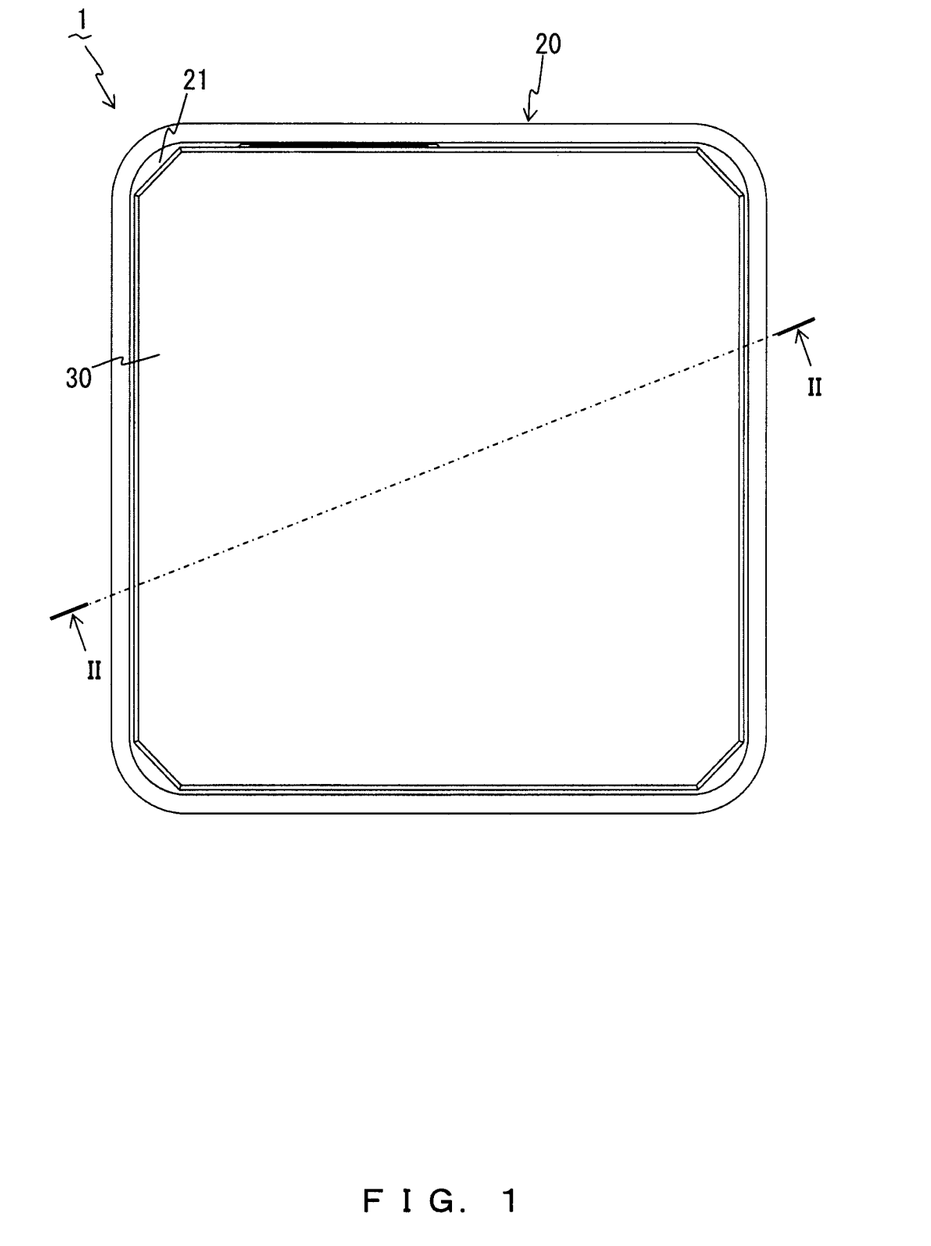
FIG. 1 is a plane view illustrating an imaging apparatus in accordance with an embodiment.

FIG. 1 is a plane view illustrating an imaging apparatus 1.

Figure 2:
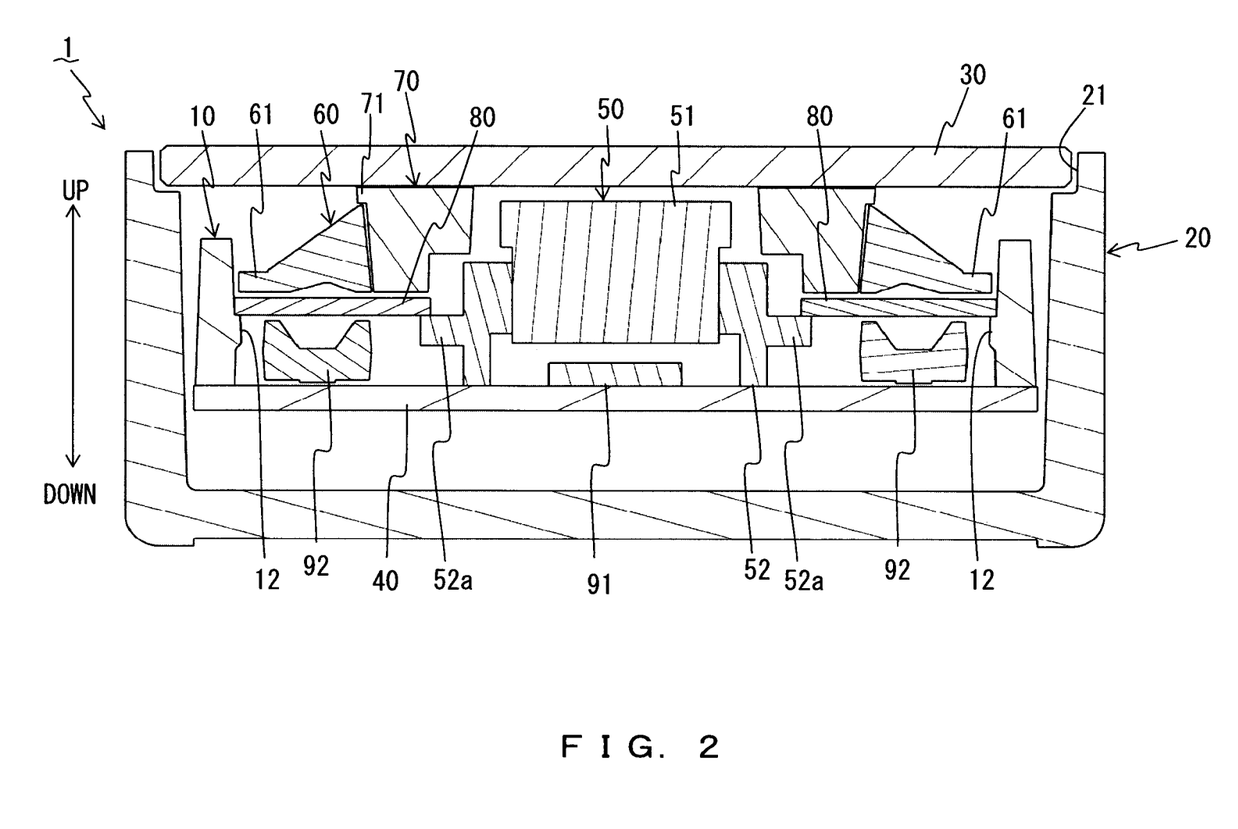
FIG. 2 is a cross-sectional view taken on line II-II of FIG. 1.

FIG. 2 is a cross-sectional view taken on line II-II of FIG. 1.

Figure 3:
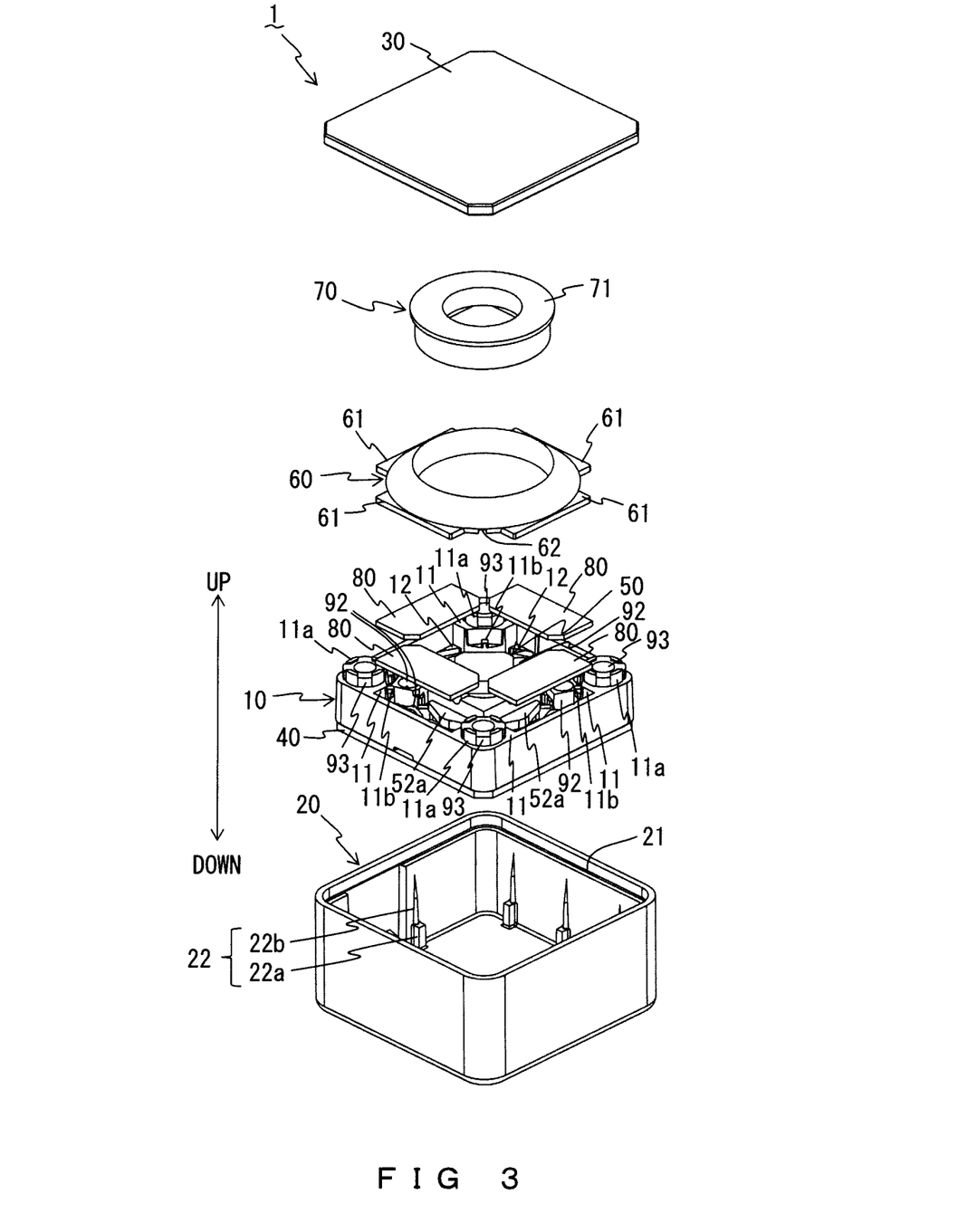
FIG. 3 is an exploded perspective view illustrating an imaging apparatus in accordance with an embodiment.

FIG. 3 is an exploded perspective view illustrating the imaging apparatus 1.

As depicted in FIGS. 2 and 3, the imaging apparatus 1 includes an aperture 10 that corresponds to an exemplary framing member, a housing 20, a top cover 30, a wiring board 40, a lens unit 50, a light guide body 60, a light shield body 70, four polarization members 80, an imaging element 91, eight illumination light emitters 92 that each correspond to an exemplary light source, and four ranging lenses 93 (see FIG. 3).

The imaging apparatus 1 is used as a biometrics authentication apparatus that performs authentication by capturing an image of a palm vein or as a portion of the biometrics authentication apparatus. However, the imaging apparatus 1 may be an imaging apparatus that captures an image of another type of biological information such as finger veins, fingerprints, or pupil irises or may be an imaging apparatus that captures an image of a subject that is not biological information.

Figure 4:
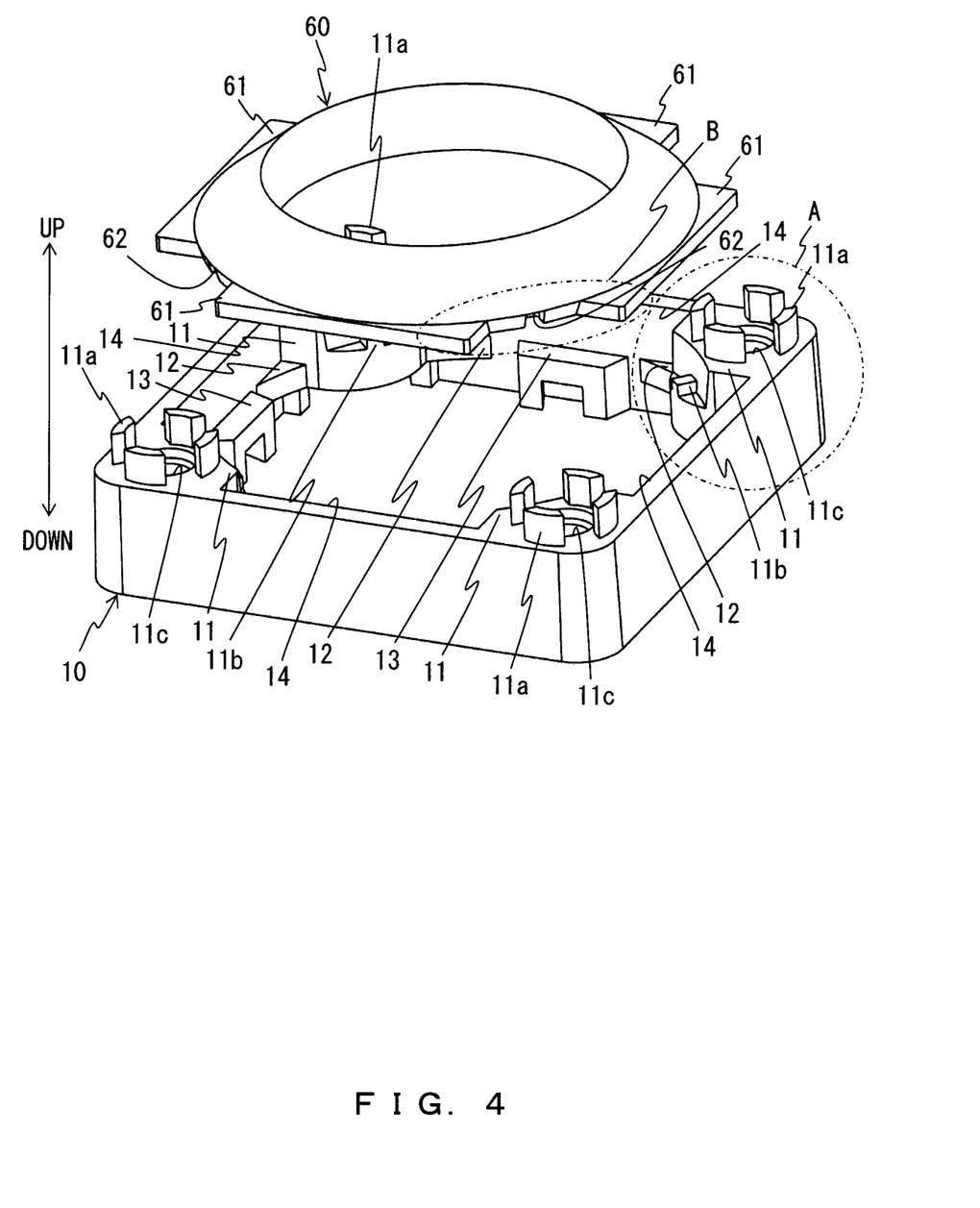
FIG. 4 is an exploded perspective view illustrating only a light guide body and an aperture in accordance with an embodiment.
Figure 5:
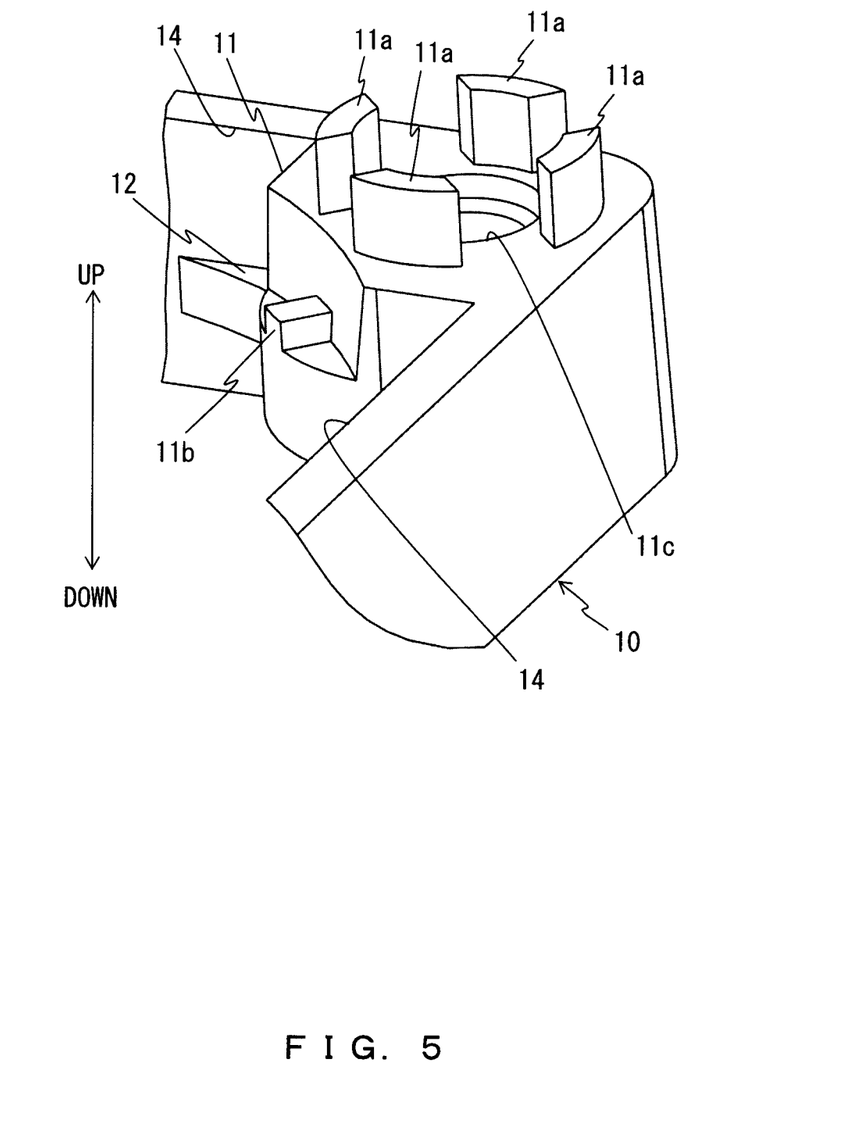
FIG. 5 is an enlarged view of a section A of FIG. 4.

As depicted in FIGS. 2-4, the aperture 10 has a frame shape (e.g., a rectangular frame shape or a rectangular hollow shape) provided on the outer edge of the wiring board 40 in such a manner as to surround the light guide body 60 and the like. As depicted in FIGS. 4 and 5, four swelling parts 11 swelling inward (toward lens unit 50) are provided at four corners of the aperture 10. The four swelling parts 11 each function as an aperture for limiting a range within which light emitted from a ranging light emitter (not illustrated) is diffused, and hence the aperture 10 may be considered to comprise four apertures integral with each other. The four apertures (swelling parts 11) may be components separate from the framing member (aperture 10).

The four swelling parts 11 each include a through hole 11c through which light emitted from the ranging light emitter passes. The ranging lens 93 illustrated in FIG. 3 is disposed over the through hole 11c of the swelling part 11. The through hole 11c is provided at each of the four swelling parts 11: the aperture 10 includes four through holes 11c in total. Expressions such as "upper", "higher", and "above" in the present embodiment correspond to a direction in which light is emitted from the illumination light emitter 92.

The swelling part 11 includes four press-fit convex parts 11a formed around the through hole 11c and projecting upward. As depicted in FIG. 3, the ranging lens 93 is press-fitted into a region surrounded by the four press-fit convex parts 11a.

An engagement convex part 11b that engages an engagement concave part 62 of the light guide body 60 depicted in FIG. 4 is provided at a portion of the swelling part 11 on the lens-unit-50 side in a manner such that the engagement convex part 11b projects upward from a portion recessed downward relative to the top surface of the aperture 10. For example, the light guide body 60 may be formed of acryl, a translucent material, and the engagement convex part 11b (aperture 10) may be formed of polycarbonate, a material less likely to be damaged than the light guide body 60. The engagement convex part 11b may be formed at a portion of the aperture 10 excluding the swelling part 11. When the aperture 10 is omitted, the engagement convex part 11b may be provided at the housing 20. In this case, the housing 20 corresponds to an exemplary framing member.

Four (a plurality of) positioning concave parts 14 into which four (a plurality of) positioning convex parts 61 of the light guide body 60 are inserted are provided at the inner surfaces of the aperture 10. The four positioning concave parts 14 are regions each sandwiched between two adjacent ones of the swelling parts 11 located at each of four edges of the aperture 10. The respective numbers of the positioning concave parts 14 and the positioning convex parts 61 may be one. When the aperture 10 is omitted, the positioning concave part 14 may be provided at the housing 20.

Eight polarization plate supporting parts 12 which are positioned to sandwich the four swelling parts 11 and on which corners of the polarization members 80 are placed are provided on the inner surfaces of the aperture 10. Meanwhile, four polarization plate supporting parts 13 on each of which a central portion of one edge of the polarization member 80 is placed are also provided on inner surfaces at the centers of four edges of the aperture 10 as seen in a plane view.

As depicted in FIGS. 2 and 3, the housing 20 has a rectangular box shape without a top surface. A concave top cover supporting portion 21 at a center side and an upper side on which the outer edge of the top cover 30 is placed is provided at an upper edge of the housing 20.

As depicted in FIG. 3, a plurality of board supporting parts 22 on which the wiring board 40 is placed are provided on the inner surface of the housing 20. The board supporting part 22 includes a supporting convex part 22a having a rectangular solid shape projecting toward the center, and a guide convex part 22b wherein portions of the guide convex part 22b located at a higher position, i.e., portions of the guide convex part 22b more distant from the supporting convex part 22a, has a smaller amount of projection. The guide convex part 22b guides onto the supporting convex part 22a the wiring board 40 inserted into the housing 20 from above together with the aperture 10. A plurality of board supporting parts 22 are provided so that the plurality of guide convex parts 22b can hold the wiring board 40 in a surrounding manner.

As depicted in FIG. 3, the top cover 30 has a rectangular plate shape. The top cover 30 is formed of a translucent material for allow passage of light such as irradiation light emitted from the illumination light emitter (e.g., a LED) 92 toward a subject (e.g., a palm vein) or reflection light from the subject. As described above, the top cover 30 is placed on the top cover supporting portion 21 at the outer edge of the housing 20 and supported by the housing 20.

As depicted in FIG. 2, the imaging element 91, the lens unit 50, the four ranging light emitters 94, and the eight illumination light emitters 92 disposed around the lens unit 50 are mounted on the wiring board 40. Mounting a part such as a central processing unit (CPU) or a memory on the wiring board 40 allows the wiring board 40 to function as a controller for the imaging apparatus 1. When the imaging apparatus 1 is used as a biometrics authentication apparatus, the wiring board 40 may function as a controller for the biometrics authentication apparatus.

As depicted in FIG. 2, the lens unit 50 includes a lens body 51 and a lens supporting member 52 for supporting a lower portion of the lens body 51, wherein the lens unit 50 focuses light on the imaging element 91.

As depicted in FIG. 3, the lens supporting member 52 includes four blocking parts 52a. The four blocking parts 52a are disposed on four side surfaces of the lens supporting member 52 having a rectangular shape when seen in a plane view and each project in such a manner as to assume an essentially triangular shape when seen in a plane view. The four blocking parts 52a each project over a region facing two of the eight illumination light emitters 92. Accordingly, the four blocking parts 52a are provided on essentially the entirety of the side surfaces of the lens unit 50. When seen in a plane view, the blocking part 52a may project over a region located around the lens unit 50 and facing the illumination light emitter 92, and, for example, may project above the illumination light emitter 92.

The blocking part 52a blocks stray light from the illumination light emitter 92. In one example, the stray light is reflected from a lower edge of the light shield body 70 depicted in FIG. 2 and then from an upper surface of the wiring board 40 and travels toward the lens body 51.

As depicted in FIG. 2, the four blocking parts 52a each have a corresponding polarization member 80 placed thereon. When the polarization member 80 is omitted from the imaging apparatus 1, another member such as the light shield body 70 may be placed on the blocking part 52a.

The light guide body 60 is toric as depicted in FIG. 4 and surrounds the lens unit 50 as depicted in FIG. 2. The light guide body 60 guides light emitted from the illumination light emitter 92 depicted in FIG. 2 to a subject through the top cover 30. The light guide body 60 desirably diffuses light emitted from the illumination light emitter 92. The top surface of the light guide body 60 is inclined downward from the inner surface of the body to the outer boundary.

Figure 7:
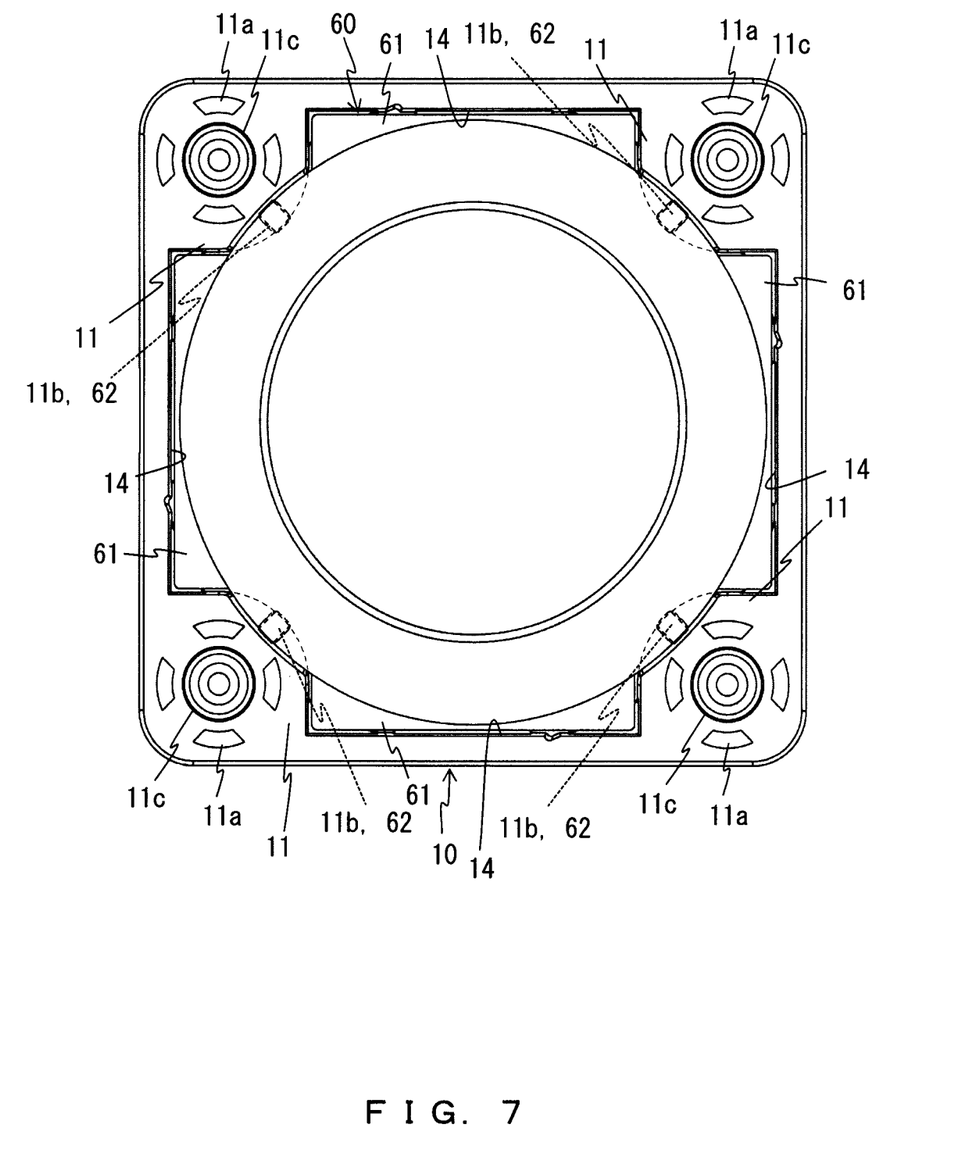
FIG. 7 is a plane view illustrating only a light guide body and an aperture in accordance with an embodiment.
Figure 8:
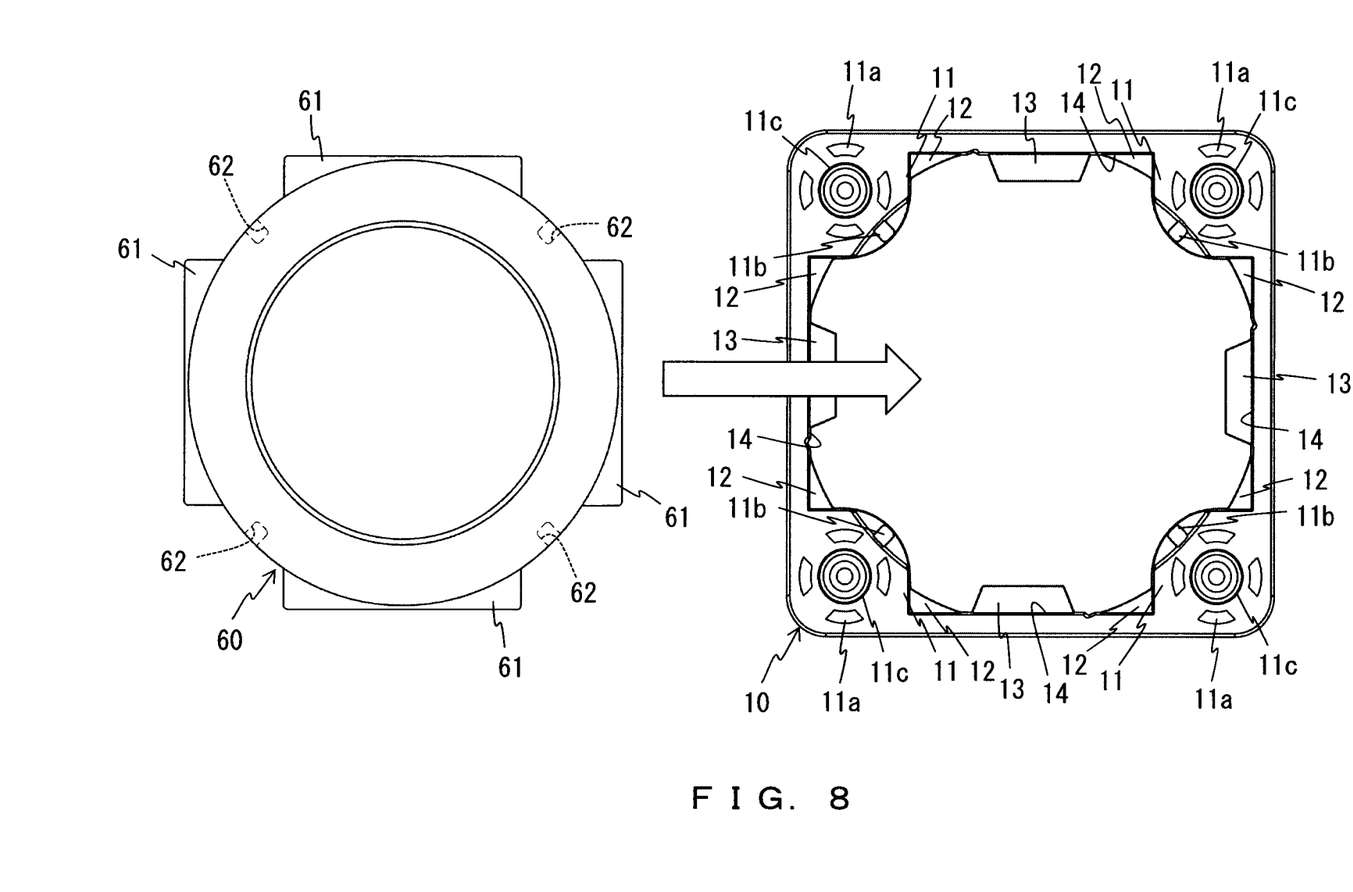
FIG. 8 is an exploded plane view illustrating only a light guide body and an aperture in accordance with an embodiment.

Four positioning convex parts (flange parts) 61 each having a rectangular plate shape project horizontally from the side surface of the light guide body 60, wherein the positioning convex parts 61 are located, with spaces therebetween, at positions rotationally symmetric with respect to the light guide body 60. The four positioning convex parts 61 are inserted into the positioning concave parts 14 from above the aperture 10 as depicted in FIGS. 7 and 8 and placed on the polarization members 80 depicted in FIGS. 2 and 3. As a result, the light guide body 60 is positioned for four arbitrary orientations arranged at 90-degree intervals. As depicted in FIG. 8, the shape of the inside of the aperture 10 as seen in a plane view is closely analogous to the outer shape of the light guide body 60 excluding the polarization plate supporting parts 12 and 13 located below the positioning convex parts 61a.

Figure 6:
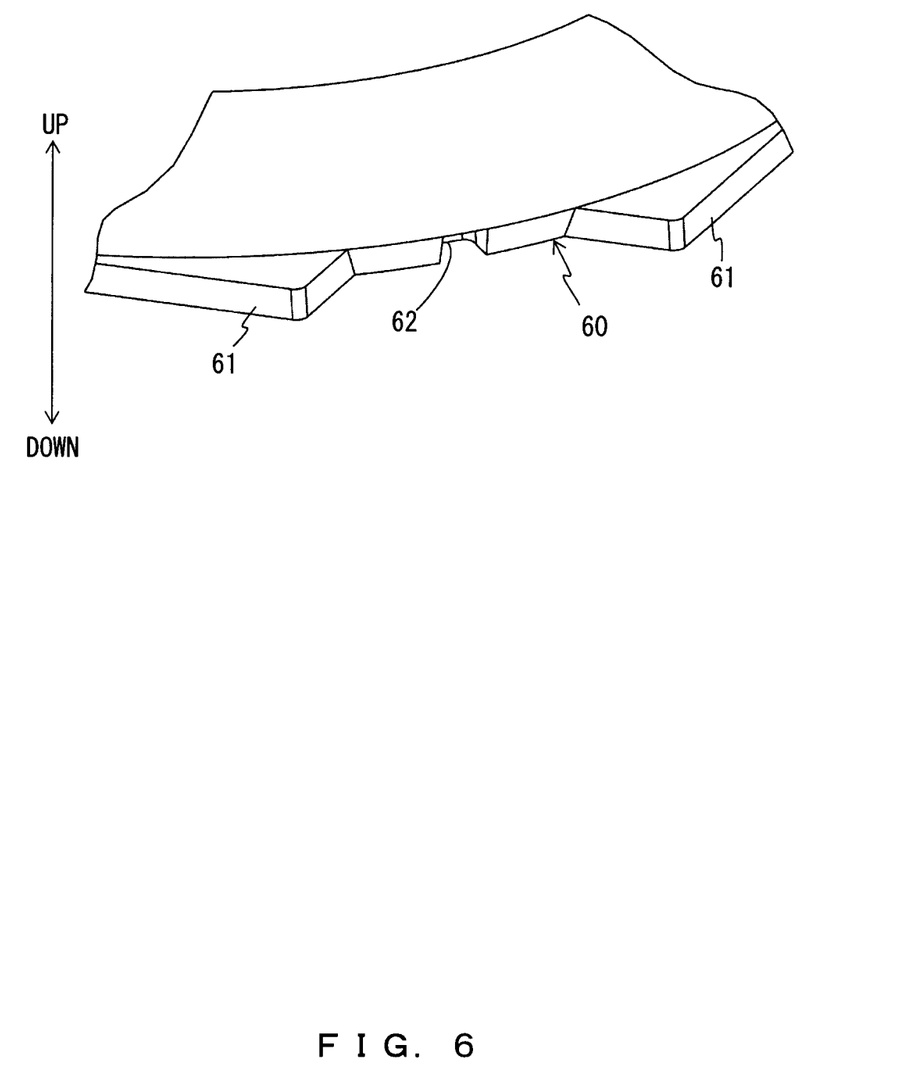
FIG. 6 is an enlarged view of a section B of FIG. 4.

As depicted in FIGS. 4 and 6, four engagement concave parts 62 are each provided on the side surface of the light guide body 60 and located between two adjacent ones of the positioning convex parts 61. As depicted in FIG. 7, the positioning convex parts 61 are inserted into the positioning concave parts 14 from above, the positioning convex parts 61 are then guided by the positioning concave parts 14, and finally the four engagement concave parts 62 engage the engagement convex parts 11b located below the upper edges of the positioning concave parts 14 (i.e., below the top surface of the aperture 10). The engagement concave parts 62 are considered to be shaped like projections and located with spaces therebetween at positions rotationally symmetric with respect to the light guide body 60, as with the positioning convex parts 61.

The light shield body 70 has a cylindrical shape as depicted in FIG. 3 and surrounds the lens body 51 so as to block light as depicted in FIG. 2. A flange part 71 projects from the entirety of the upper edge of the side surface of the light shield body 70. The light shield body 70 is sent to the inside of the light guide body 60 from above, and the flange part 71 is placed on the light guide body 60.

As described above, the four polarization members 80 are each placed on one blocking part 52a of the lens unit 50 and on two polarization plate supporting parts 12 and one polarization plate supporting part 13 of the aperture 10. As a result, as depicted in FIG. 2, the four polarization members 80 are located on an optical path of light emitted from the illumination light emitter 92, i.e., located above the illumination light emitter 92.

In the embodiment described above, the imaging apparatus 1 includes an imaging element 91, a lens unit 50 that focuses light on the imaging element 91, eight illumination light emitters 92 that correspond to exemplary light sources disposed around the lens unit 50, a light guide body 60 that surrounds the lens unit 50 and that guides light emitted from the eight illumination light emitters 92, and an aperture 10 that corresponds to an exemplary framing member surrounding the light guide body 60. The light guide body 60 is provided with engagement concave parts 62 that engage the engagement convex parts 11b provided at the aperture 10.

In the meantime, the light guide body 60 is a member for guiding light and is thus formed of a material such as acryl that is easily damaged. Accordingly, the light guide body 60 includes, as engagement parts, engagement concave parts 62 rather than engagement convex parts, so that if the imaging apparatus 1 has been subject to a dropping impact, the engagement concave parts 62 of the light guide body 60 can be prevented from being damaged, in comparison with a situation in which engagement convex parts are provided. In this way, the present embodiment allows the engagement part of the light guide body 60 to be prevented from being damaged. It is difficult to visually check the color of the light guide body 60 because the light guide body 60 is a member for guiding light. Accordingly, engagement convex parts 11b are provided at the aperture 10, not at the light guide body 60, so that the engagement convex parts 11b can be easily visually checked. Thus, the imaging apparatus 1 can be easily assembled.

In the present embodiment, the light guide body 60 includes positioning convex parts 61 projecting from the side surface of the light guide body 60, and the aperture 10 includes positioning concave parts 14 into which the positioning convex parts 61 are inserted. Hence, the light guide body 60 and the aperture 10 can not only simply engage each other but also can be positioned before the engaging; accordingly, the light guide body 60 and the aperture 10 can be made to engage each other without checking the positions of the engagement concave parts 62 of the light guide body 60 and the engagement convex parts 11b of the aperture 10. Thus, the imaging apparatus 1 can be assembled more easily. The positioning convex parts 61 are used for positioning and thus unlikely to adversely affect the engagement of the light guide body 60 and the aperture 10 even if the positioning convex parts 61 are damaged.

In the present embodiment, the light guide body 60 is toric, the light guide body 60 includes a plurality of positioning convex parts 61 at positions rotationally symmetric with respect to the light guide body 60, and the aperture 10 includes a plurality of positioning concave parts 14 into which the plurality of positioning convex parts 61 are inserted. This allows the light guide body 60 to be positioned at any position with reference to the rotation direction of the light guide body 60.

In the present embodiment, the aperture 10 has a rectangular frame shape, swelling parts 11 swelling toward the center of the aperture 10 are formed at four corners of the aperture 10, the plurality of positioning concave parts 14 of the aperture 10 are regions each sandwiched between two adjacent ones of the swelling parts 11 located at each of four edges of the aperture 10. This simplifies the configuration of the imaging apparatus 1.

In the present embodiment, the engagement convex part 11b of the aperture 10 is provided at the swelling part 11. This further simplifies the configuration of the imaging apparatus 1.

In the present embodiment, the imaging apparatus 1 further includes ranging lenses 93 disposed at the swelling parts 11, and the swelling parts 11 each include a through hole 11c through which light for distance measurement passes. This further simplifies the configuration of the imaging apparatus 1.

The present invention is not limited to the described embodiments and can be embodied by making changes to the components without departing from the gist of the invention in an implementation phase. Various inventions can be formed by combining, as appropriate, a plurality of components disclosed with reference to an embodiment. For example, all of the components indicated in an embodiment may be combined as appropriate. In this way, various changes or applications are possible without departing from the spirit of the invention.

The invention claimed is:

1. An imaging apparatus comprising:
an imaging element;
a lens unit that focuses light on the imaging element;
a light source located around the lens unit;
a light guide body that surrounds the lens unit and that guides light emitted from the light source; and
a framing member surrounding the light guide body and having a rectangular frame shape, wherein
the light guide body includes an engagement concave part that engages an engagement convex part of the framing member,
swelling parts swelling toward a center of the framing member are formed at four corners of the framing member, and
the engagement convex part of the framing member is provided so as to project at each of the swelling parts in a direction in which light is emitted from the light source.

2. The imaging apparatus of claim 1, further comprising:
ranging lenses disposed at the swelling parts, wherein
the swelling parts each include a through hole through which light for distance measurement passes.

3. The imaging apparatus of claim 1, wherein
the light guide body includes a positioning convex part projecting from a side surface of the light guide body, and
the framing member includes a positioning concave part into which the positioning convex part is inserted.

4. The imaging apparatus of claim 3, wherein
the light guide body is toric,
the light guide body includes a plurality of said positioning convex parts at positions rotationally symmetric with respect to the light guide body, and the framing member includes a plurality of said positioning concave parts through which the plurality of positioning convex parts are inserted.

5. The imaging apparatus of claim 4, wherein
the plurality of positioning concave parts of the framing member are regions each sandwiched between two adjacent ones of the swelling parts located at each of four edges of the framing member.

* * * * *